United States Patent [19]
Tuneberg

[11] Patent Number: 5,756,174
[45] Date of Patent: May 26, 1998

[54] BOND CARD

[75] Inventor: Lee H. Tuneberg, Sheboygan, Wis.

[73] Assignee: American Orthodontics Corporation, Sheboygan, Wis.

[21] Appl. No.: 716,628

[22] Filed: Sep. 20, 1996

Related U.S. Application Data

[60] Provisional application No. 60/012,004, Feb. 21, 1996.

[51] Int. Cl.$^6$ .................................................. A61C 3/00
[52] U.S. Cl. ...................... 428/40.1; 428/41.7; 428/41.8; 428/42.1; 428/42.2; 428/42.3; 433/8; 433/9; 433/10
[58] Field of Search .................... 428/40.1, 41.7, 428/41.8, 42.1, 42.2, 42.3; 433/8, 9, 10

[56] References Cited

U.S. PATENT DOCUMENTS

| | | | |
|---|---|---|---|
| 4,978,007 | 12/1990 | Jacobs et al. | 206/469 |
| 5,015,180 | 5/1991 | Randklev | 433/9 |
| 5,172,809 | 12/1992 | Jacobs et al. | 206/368 |
| 5,221,202 | 6/1993 | James | 433/9 |
| 5,328,363 | 7/1994 | Chester et al. | 433/9 |
| 5,348,154 | 9/1994 | Jacobs et al. | 206/369 |
| 5,350,059 | 9/1994 | Chester | 433/9 |
| 5,542,844 | 8/1996 | Perret, Jr. | 433/9 |
| 5,575,645 | 11/1996 | Jacobs | 433/9 |

*Primary Examiner*—Nasser Ahmad
*Attorney, Agent, or Firm*—Lloyd L. Zickert

[57] ABSTRACT

A bond card for mounting prepasted orthodontic appliances that includes a substantially rigid planar substrate and a flexible adhesive-releasing film attached to the substrate and having a plurality of unmounted or unattached portions serving as sites for the appliances that are capable of being lifted from the surface of the substrate to facilitate removal of the appliance for mounting on a tooth.

17 Claims, 1 Drawing Sheet

BOND CARD

This application claims the benefit of U.S. provisional application No. 06/012,004, filed Feb 21, 1996 pending.

DESCRIPTION

This application is based on the provisional application Serial No. 60/012,004, filed Feb. 21, 1996. This invention relates in the general to a new and improved bond card for use in organizing a series of orthodontic appliances such as brackets for mounting on a patient's teeth, wherein the brackets are prepasted, and more particularly to a bond card having a substantially rigid planar substrate and on which a flexible film is attached and including unattached portions on which the prepasted appliances are initially mounted.

BACKGROUND OF THE INVENTION

Heretofore, it has been well known to provide bond cards for organizing a set of orthodontic appliances to be mounted on the teeth of a patient, wherein a plurality of appliances such as brackets and/or buccal tubes may be prepasted with light-curable adhesive and release mounted on the bond card. Particularly, the bond card has been provided with a layer of adhesive-releasing material, such as a polyester or a polytetrafluorethylene material, wherein the adhesive surface of the appliance may be easily separated from the flexible film. When removing the appliance from the bond card to be placed in the mouth of a patient, difficulty is sometimes encountered in the removal of the appliance from the bond card when lifting the appliance from the card, which may cause a problem with respect to the integrity of the adhesive on the appliance, wherein the adhesive needs to be reformed.

It has also been known, as disclosed in U.S. Pat. No. 5,328,363, to provide a package for prepasted orthodontic appliances which includes wells or recesses into which the appliances are received and enclosed, and wherein a flexible film arrangement is provided in the wells to which the appliance may be movably attached to a flexible part of the film to enhance the peeling of a prepasted appliance from the film. It will be understood that a prepasted appliance is one having an adhesive applied to the side to be mounted on a tooth.

SUMMARY OF THE INVENTION

The present invention relates to a new and improved bond card for receiving a plurality of prepasted appliances that may be provided with a light-curable adhesive of a viscosity which allows the adhesive to be peeled from the bond card without distorting the adhesive on the appliance. Thus, the bond card of the invention is especially useful to an orthodontist wanting to prepaste appliances and mount and store the appliances on a bond card prior to removing the appliances from the bond card at chairside to mount on a patient's teeth. It is important that any adhesive on an appliance be substantially over the entire surface that is to be mounted to a tooth and to remain intact once the appliance with adhesive is removed from the bond card. Accordingly, preferred adhesives are those that will maintain the best possible shape following application to the bracket base, mounting on a substrate like a bond card, and then removing it from the bond card for application and bonding to the tooth.

The bond card of this invention is unique in that it includes a feature that allows a bracket to easily separate from the card and maintain the adhesive intact. This feature is provided by including a bond card having a substantially rigid substrate that is planar in form and securing on the substrate a flexible film having an adhesive-releasing portion that is anchored to the card but free to be lifted above the card so as to facilitate separation between adhesive on the appliance when a lifting force is applied to the appliance to peel the appliance free. A flexible film may be of a suitable polyester or polytetrafluorethylene material having the adhesive-releasing capability which would minimize, if not eliminate, any residue of the adhesive remaining on the film when the adhesive-backed appliance is removed from the film and which would not tend to distort the adhesive as applied to the backside of the appliance.

It is therefore an object of the present invention to provide a new and improved bond card for use in handling prepasted orthodontic appliances such as brackets, and more particularly to a bond card capable of handling adhesives of lower viscosity which are sometimes preferred by orthodontists.

Another object of the present invention is to provide a bond card having a substantially rigid planar substrate and a flexible film mounted thereon which is secured so that it provides a portion that is capable of being lifted from the surface of the substrate and on which it may receive an adhesive-backed appliance whereby the free portion of the film facilitates separation of the adhesive from the film when a removal force is applied to the appliance.

Other objects, features and advantages of the invention will be apparent from the following detailed disclosure, taken in conjunction with the accompanying sheet of drawings, wherein like reference numerals refer to like parts.

DESCRIPTION OF THE INVENTION

Figure 1:
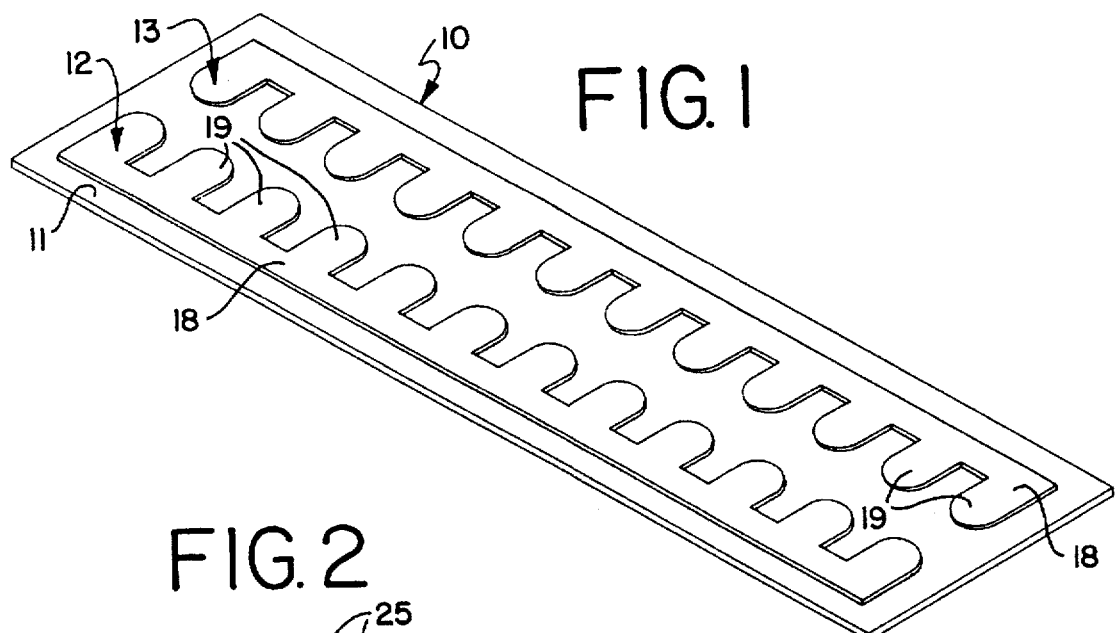
FIG. 1 is a perspective view of a bond card according to the invention.
Figure 2:
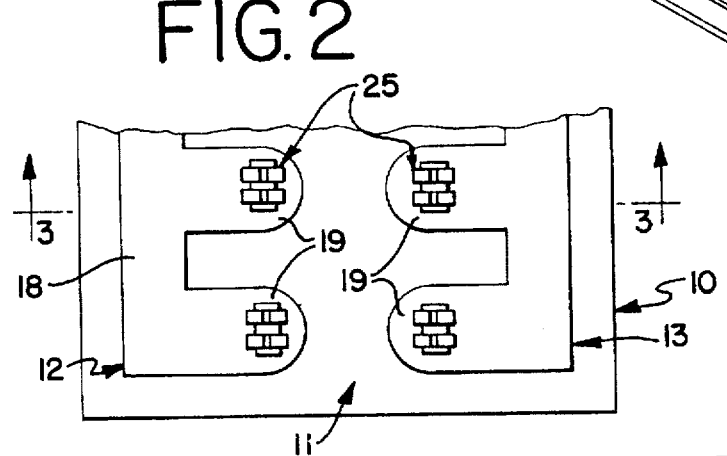
FIG. 2 is a fragmentary enlarged top plan view of the bond card in FIG. 1 with orthodontic brackets mounted in place on the unattached portion of the adhesive-releasing flexible film.
Figure 3:
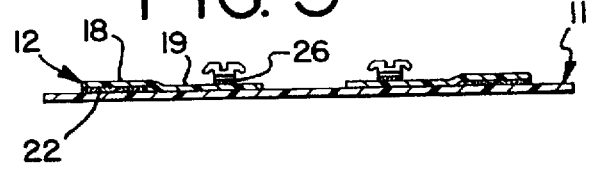
FIG. 3 is an enlarged transverse sectional view taken substantially along line 3—3 of FIG. 2.

Referring now to the drawings, and particularly to FIGS. 1 to 3, the bond card of the present invention is generally designated by the numeral 10 and includes a substantially planar and rigid substrate 11 and first and second strips of flexible film 12 and 13 mounted on the substrate 11.

The substrate is preferably made of a material that will provide a sufficient rigidity that it can easily be handled and be self-supporting if engaged by opposite edges or at the end, and that would remain substantially flat on a supporting surface if held in place by a person while removing brackets. It may be made of a suitable cardboard, a high-density polyethylene, a polystyrene, or any other suitable material, and of a suitable thickness to provide the desired rigidity.

The flexible film may be made of any suitable material that has good adhesive-releasing characteristics, such as a silicone, polyethylene, polyester, or a fluoropolymer such as a polytetrafluorethylene. One satisfactory type of polyester film is a Mylar film sold by DuPont. Mylar is a trademark of DuPont for a polyester film. Such a polyester film may have a suitable thickness to allow the film to properly function as below described. Another suitable type of film would be one made by DuPont under the trademark Teflon, which is a trademark for a polytetrafluorethylene (TFE) fluorocarbon polymer material.

The flexible films 12 and 13 are identical except they are preferably applied as shown in FIG. 1. Each film includes an anchored or secured portion 18 and a plurality of fingers or projections 19 which constitute the unattached portions of the flexible film. The anchored or attached portion 18 is secured to the substrate 11 by a suitable cured adhesive 22, as shown particularly in FIG. 3. Thus, the fingers 19 of the flexible film are unattached to the substrate 11 except by the anchored portion 18. These fingers are sized so that they can easily receive an orthodontic attachment and completely cover the adhesive on the base of such an attachment.

As illustrated, each flexible film includes twelve fingers 19 which will provide enough for receiving a usual number of appliances. However, a greater or lesser number of fingers may be used if desired. The orthodontic attachments or appliances illustrated are orthodontic brackets 25 and these brackets include an adhesive or bonding material 26 on the backside, which would be adapted to contact the tooth of a patient to mount the bracket on a tooth. Preferably, the bonding material or adhesive would be light-curable, and it will be appreciated that the bond card with the brackets having light-curable adhesive would be stored in a container that would shield the adhesive from natural or artificial light, and further that when the bond card with the brackets attached thereto is used at chairside, a cover member could be used to overlie the card and prevent light from reaching the adhesive that would cause it to cure, as disclosed in my copending application Ser. No. 08/580,601, filed Dec. 29, 1995. Further, the adhesive would have a viscosity such that it can be peeled from the bond card without disturbing the attachment and form of the adhesive to the bracket.

Application of adhesive to the bracket would leave it in a sticky state so that it could stick to the flexible film when mounted thereon but thereafter be separated from the film when it is desired to transfer the bracket to the tooth of a patient.

It will be understood that the adhesive 22 for attaching the flexible films to the substrate will be of a type to permanently attach the film to the substrate at the area where the adhesive is located. Any suitable adhesive that will accomplish this result may be used.

Figure 4:
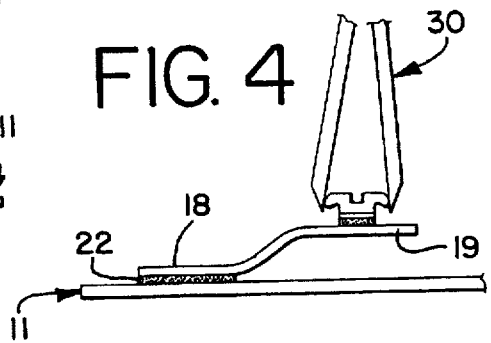
FIG. 4 is a diagrammatic side elevational view illustrating the operation of the flexible portion of the flexible film when a force is applied to the bracket to remove it from the bond card.

As illustrated in the drawings, each finger 19 of the flexible films 12 and 13 provides a site on which a prepasted appliance may be mounted. When it is desired to remove the appliance from the bond card, a suitable instrument such as a tweezers 30 may be used to engage the bracket to lift it from the bond card. As the bracket is lifted upwardly, as shown in FIG. 4, the unattached finger 19 will also come up with the bracket until the portion of the finger between the anchored portion 18 and the bracket is taut and then further lifting of the bracket will cause peeling of the bracket from the finger, starting at the edge of the adhesive adjacent to the anchored portion 18 of the flexible film. Then the bracket will just peel away from the finger without disturbing the make-up of the adhesive and maintaining the adhesive intact so that it can be directly applied to a tooth without the necessity of reforming the adhesive on the back of the bracket. As the bracket is removed, it will be appreciated that the unattached portion of the flexible film will somewhat curl and take the general form of a crawling snake before the bracket is separated from the film. The peeling action between the adhesive and the flexible film as caused by the action of the unattached portion facilitates the separation of the adhesive 26 from the adhesive-releasing film leaving the adhesive in substantially the same form as when it was applied to the bracket, so that it will thereafter properly serve to provide the best possible bonding to a tooth. Preferably, the distance between the anchored portion 18 of the flexible film and the adjacent edge of the bracket at the adhesive is such that lifting of the bracket and cycling through the peeling of the bracket from the flexible finger will be facilitated.

Figure 5:
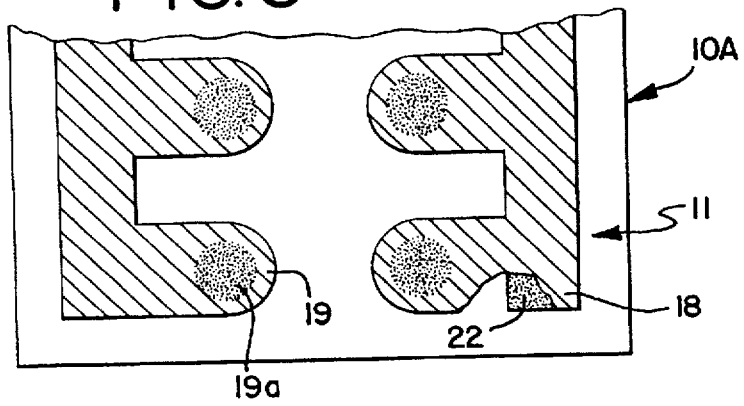
FIG. 5 is a fragmentary enlarged plan view of a further bond card having indication means as to where the prepasted appliance is to be mounted so as to assure that it is on the loose or free portion of the adhesive-releasing film.

A modified bonding card is shown in FIG. 5 and designated as 10A that only differs from the embodiment of FIG. 1 in that colored areas 19a are applied to the fingers 19 of the flexible films in order to designate the site where the appliance may be mounted such that it may be efficiently peeled from the finger as above described. This colored area would be of a different color than the color of the flexible film so as to clearly mark the site where the appliance is to be initially mounted.

A further alternative embodiment of the bond card of the present invention includes a substantially rigid planar substrate and a single strip of flexible film mounted on the substrate. The single strip of flexible film has a central portion which is secured to the substrate and a plurality of opposing fingers or projections extending from opposite sides of the central portion. The fingers constitute the unattached portions of the flexible film. This embodiment simplifies manufacturing and construction of the bond card of the present invention.

It should be further appreciated that a flexible film of any material may be used which would include an adhesive-releasing site on a portion that can be lifted from the substrate. Further, indicia may be added to the substrate or the flexible film to identify the tooth on which a bracket is to be mounted.

While not shown, it should be further appreciated that individual fingers or strips for an attachment could be used rather than fingers attached to a common anchoring portion. Then each strip would include an anchoring portion permanently secured to the substrate and an unattached portion extending from the anchoring portion.

It will be understood that modifications and variations may be effected without departing from the scope of the novel concepts of the present invention, but it is understood that this application is to be limited only by the scope of the appended claims.

The invention is hereby claimed as follows:

1. An orthodontic bond card for mounting a plurality of orthodontic appliances having uncured adhesive on their mounting surfaces which comprises:

a substantially rigid planar substrate, a single, unitary, flexible adhesive-releasing film including an attachable portion and a plurality of unattachable portions extending from the attachable poriton for receiving the prepasted orthodontic appliances, and means attaching said attachable portion to said substrate.

2. The bond card of claim 1, wherein said unattachable portions extend from one side of said attachable portion.

3. The bond card of claim 2, wherein said unattachable portions extend from opposite sides of said attachable portion.

4. The bond card of claim 1, wherein said unattachable portions have colored areas to designate the proper placement of the appliances thereon.

5. The bond card of claim 1, which includes a second single, unitary flexible adhesive-releasing film having an attachable portion secured to the substrate and a plurality of unattachable portions extending from the attachable portion for mounting prepasted appliances thereon.

6. An orthodontic bond card for receiving a plurality of orthodontic appliances having uncured adhesive on their mounting surfaces which comprises:

a substantially rigid planar substrate, at least one adhesive-releasing single, unitary flexible film for receiving appliances, and means attaching a portion of said film to said substrate, said film including a plurality of unattached portions extending from an attached portion for receiving the appliances, said attached portion being attached to the substrate, whereby removal of the appliances from the film is facilitated by the coaction between the appliances and the unattached portion as a separating force is applied to the appliances.

7. The bond card of claim 6, wherein the adhesive is light-curable and the entire substantially rigid planar substrate is adapted to be inserted into a container for shielding the adhesive from natural or artificial light.

8. The bond card of claim 6, wherein the substrate is self-supporting when engaged by opposite edges or at an end.

9. The bond card of claim 8, wherein the substrate remains substantially flat on a supporting surface when the appliances are removed.

10. An orthodontic bond card for removably receiving a plurality of orthodontic brackets with bases having light-curable adhesive thereon, said bond card comprising:

a planar substantially rigid substrate, a single, unitary, flexible adhesive releasing film having a first portion secured to the substrate and having a plurality of unattached second portions extending from the first portion, said second portions not being secured to the substrate and defining sites for receiving the adhesive bases of the brackets, whereby the brackets may be easily peeled or separated from the second portions which are initially lifted from the substrate upon engagement and lifting of the brackets and thereafter the base adhesive peels from the film starting at one edge of the adhesive.

11. The bond card of claim 10, wherein the bond card includes a second single, unitary, flexible adhesive releasing film having a first portion secured to the substrate and having a plurality of second unattached portions extending from the first portion, said second portions not being secured to the substrate and defining sites for receiving the adhesive bases of the brackets, whereby the brackets may be easily peeled or separated from the second portions which are initially lifted from the substrate upon engagement and lifting of the brackets and thereafter the base adhesive peels from the film starting at one edge of the adhesive.

12. The bond card of claim 11, wherein the second portions on the first and second films extend from one side of said first portions of the first and second films.

13. The bond card of claim 12, wherein the first and second films are attached to the substrate with the plurality of the second portions in alignment with each other.

14. The bond card of claim 13, wherein the substrate is self-supporting when engaged by opposite edges or sides or at an end.

15. An orthodontic bond card for mounting prepasted orthodontic appliances which comprises:

a substantially rigid planar substrate, said substrate being self-supporting when engaged by opposite edges or sides or at an end, at least one single, unitary, flexible film attached to the substrate having an anchored portion and a plurality of unattached portions extending from the anchored portion, and adhesive releasing means on the unattached portions defining sites for receiving the adhesive side of prepasted appliances, whereby removal of an appliance is facilitated by the action between the adhesive side of the appliance and the unattached portion.

16. The bond card of claim 15, wherein the anchored portion extends and is secured substantially along the entire length of the substrate.

17. The bond card of claim 15, which includes a second single, unitary, flexible adhesive-releasing film having an attachable portion secured to the substrate and a plurality of unattachable portions extending from the attachable portion for mounting prepasted appliances thereon.

* * * * *